United States Patent [19]

Lichtenfels, II et al.

[11] Patent Number: 5,379,658
[45] Date of Patent: Jan. 10, 1995

[54] INTRUSIVE ACOUSTIC SENSOR MOUNTING ARRANGEMENT

[75] Inventors: Frederick L. Lichtenfels, II, Vergennes; Frederick G. Hoff, Bristol, both of Vt.

[73] Assignee: Simmonds Precision Products, Inc., Akron, Ohio

[21] Appl. No.: 976,612

[22] Filed: Nov. 16, 1992

[51] Int. Cl.⁶ .................................... G01L 19/00
[52] U.S. Cl. ........................... 73/866.5; 73/644
[58] Field of Search ............. 73/149, 32 A, 597, 624, 73/644, 290 V, 866.5; 367/908; 310/335, 336, 348

[56] References Cited

U.S. PATENT DOCUMENTS

| | | | |
|---|---|---|---|
| 1,933,979 | 11/1933 | Hentschel | 310/348 |
| 3,596,504 | 8/1971 | Frey | 73/67.8 |
| 4,130,018 | 12/1978 | Adams et al. | 73/290 |
| 4,365,515 | 12/1982 | Abts | 73/632 |
| 4,505,160 | 3/1985 | Zacharias, Jr. | 310/336 |
| 4,570,483 | 2/1986 | Sobue | 73/290 |
| 4,625,570 | 12/1986 | Witherspoon et al. | 73/863.81 |
| 4,628,732 | 12/1986 | Makinen | 73/866.5 |
| 4,640,126 | 2/1987 | Jansch | 73/290 |
| 4,640,128 | 2/1987 | Lewis | 73/866.5 |
| 4,752,178 | 6/1988 | Greenhill | 411/521 |
| 4,770,038 | 9/1988 | Zucherwar et al. | 73/290 V |
| 4,806,902 | 2/1989 | Gana | 340/59 |
| 4,850,213 | 7/1989 | Steinebrunner | 73/290 |
| 4,854,181 | 8/1989 | Gerstel | 73/863.86 |
| 4,901,245 | 2/1990 | Olson et al. | 73/290 V |
| 4,901,776 | 2/1990 | Attinello | 141/95 |
| 4,958,527 | 9/1990 | Couvillion | 73/863.86 |
| 4,984,449 | 1/1991 | Caldwell et al. | 73/49.2 |
| 5,172,594 | 12/1992 | Dyke | 73/290 V |
| 5,186,050 | 2/1993 | Lagace et al. | 73/866.5 |

*Primary Examiner*—Robert Raevis
*Attorney, Agent, or Firm*—Leonard L. Lewis; William E. Zitelli

[57] ABSTRACT

An intrusive mounting arrangement for an acoustic sensor includes an acoustic window and a flange assembly for mounting the sensor and window on a fluid tank, the flange assembly having a body portion configured to extend through an opening in the tank wall in a fluid-tight manner into the tank interior, the flange assembly having a body flange that is attachable to the tank wall; the body portion having a fluid passageway therein and a port that permits fluid in the tank to flow into the passageway; the flange assembly further comprising means for retaining the acoustic window in the passageway; the sensor comprising a body that is insertable in the fluid passageway in a fluid-tight manner; the sensor further comprising an active surface acoustically coupled to the window by fluid when the sensor is fully inserted in the passageway.

24 Claims, 1 Drawing Sheet

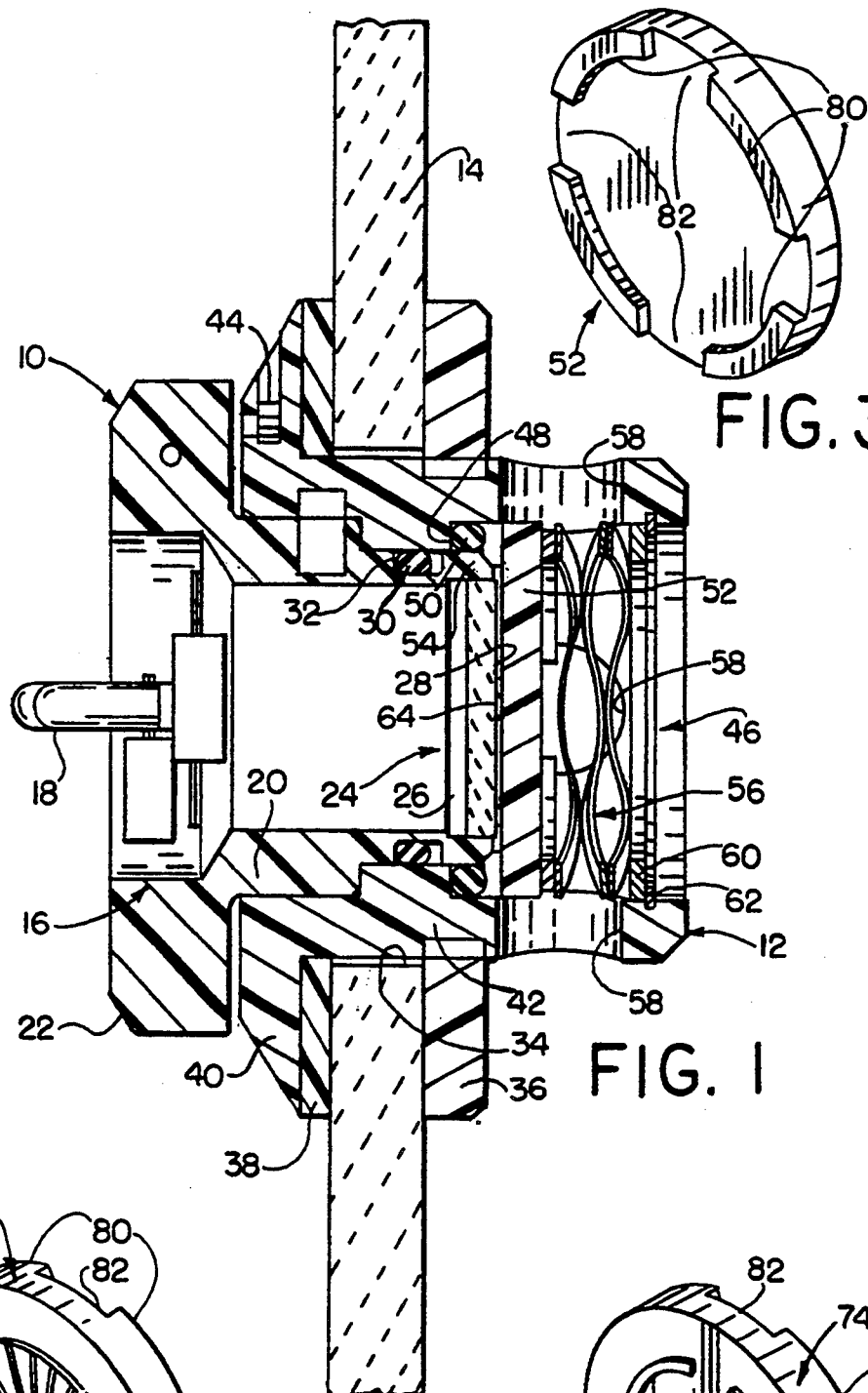
FIG. 3
FIG. 1
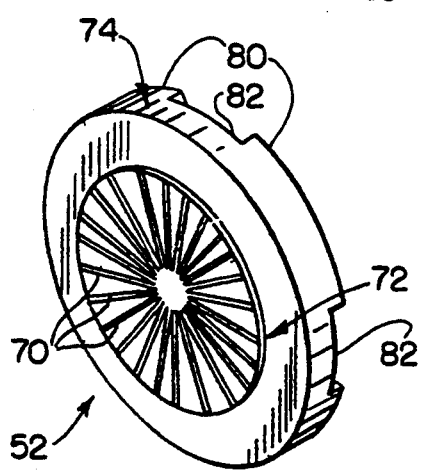
FIG. 2A
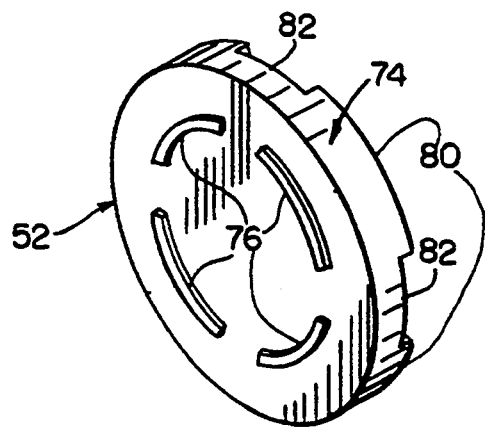
FIG. 2B

INTRUSIVE ACOUSTIC SENSOR MOUNTING ARRANGEMENT

BACKGROUND OF THE INVENTION

The invention relates generally to fluid level sensors, such as acoustic transducers that emit and receive acoustic pulses. More particularly, the invention relates to techniques for mounting ultrasonic fluid level sensors or other electronic devices in a container in an intrusive arrangement so that the fluid in the container wets the device or transducer active surface.

The use of acoustic transducers for determining fluid levels in containers is well known. In one form of use known as intrusive, an acoustic transducer is mounted within the container so that the transducer emits the acoustic pulses directly into the fluid. Usually, a still-well is used to reduce the effects of the fluid swashing around the transducer, as well as to provide a channel for the acoustic waves to follow to the surface of the fluid.

A typical application of an intrusive transducer is with fuel tanks used on aircraft. By mounting a transducer at the bottom of a tank, the transducer can be used to emit pulses towards the fuel surface. The round trip time for the acoustic energy to be reflected back to the transducer can be correlated with the fuel height when the velocity of the acoustic pulses in the fuel is known.

Numerous problems are encountered with the known fuel sensor mounting arrangements. Among them is the fact that sensors typically are mounted to the tank in such a manner that in order to remove a sensor (such as for repair or replacement during routine maintenance the fuel must first be removed from the tank. Draining the fuel for simple repair or replacement of a sensor is an expensive and time consuming task. In other mounting arrangements, the sensors are fixed to the tank wall, thus not only requiring draining the fuel but also an extensive tear down of the fuel tank.

The next generation aircraft are expected to make extensive use of composite materials for the wings. In circumstances where the wing also serves as the fuel tank, tear down for sensor replacement will not be acceptable maintenance practice.

The need exists, therefore, for an intrusive sensor mounting arrangement that permits quick and easy sensor installation and removal without needing to drain the fuel prior to sensor removal. The mounting arrangement should also provide minimal fuel displacement from the fuel tank when a sensor is removed; and the sensor should be installable and removable without tank or structural tear down or damage.

SUMMARY OF THE INVENTION

In view of the aforementioned problems with previous mounting arrangements, the invention contemplates an acoustic sensor mounting apparatus and method which, in a preferred embodiment, comprises a flange assembly attachable to the tank wall and having a fluid passageway therein, the sensor being adapted to mate and unmate with the flange assembly in the fluid passageway, the sensor being wetted by fluid when mated to the flange assembly, and the flange assembly comprising means for preventing fluid loss when the sensor is unmated therefrom. The preferred intrusive mounting method comprises the steps of mounting a flange assembly having a fluid passageway at a through hole in the fluid tank in a fluid-tight manner; sealing the flange assembly passageway to prevent fluid loss when the sensor is uncoupled from the flange assembly; and permitting fluid flow into the passageway when the sensor is coupled to the flange assembly to permit fluid to wet an acoustic element of the sensor.

These and other aspects and advantages of the present invention will be readily understood and appreciated by those skilled in the art from the following detailed description of the preferred embodiments as the best mode contemplated for carrying out the invention, in view of the accompanying drawings.

BRIEF DESCRIPTION OF THE DRAWINGS

FIG. 1 is a longitudinal section of a mounting arrangement according to the present invention;

FIGS. 2A and 2B are perspectives of alternative designs for acoustic windows suitable for use with the invention; and FIG. 3 is an opposite view perspective of an acoustic window such as shown in FIGS. 2A and 2B.

DETAILED DESCRIPTION OF THE INVENTION AND PREFERRED EMBODIMENTS

The present invention contemplates in a general sense a mounting technique for positioning an electronic device inside a fluid container such that the device can easily be installed and removed without significant loss of fluid from the container. The invention is particularly useful for intrusive installation of a device within a container such that the device is directly exposed to the fluid therein. As an example, the invention has been found to be particularly useful for intrusive installation of an ultrasonic fuel level sensor inside an aircraft fuel tank. Although the preferred embodiments of the invention are described herein with reference to such a specific application, it will be readily appreciated that the invention can similarly be used in different situations that impose intrusive mounting requirements for an electronic device.

With reference now to FIG. 1, a first embodiment of the invention is illustrated in partial cross-section. An ultrasonic transducer or sensor assembly is generally indicated with the numeral 10. The transducer 10 is mechanically matable with a mounting flange assembly 12. The sensor assembly 10 can be conveniently mated with the flange assembly 12 by a threaded connection, a bayonet-type connection, or other suitable arrangement. The mounting flange 12 is rigidly mounted to a wall 14 of a fluid container, such as, for example, a bottom wall portion of an aircraft fuel tank.

The sensor assembly 10 may include a potted electronics portion 16 with a pigtail or cable connection 18 for supplying electrical power and signal lines. The sensor assembly 10 includes a body 20 that is provided with an external nut 22 to facilitate a threaded engagement with the flange assembly 12.

The sensor assembly 10 further includes an acoustic element 24 such as, for example, a piezoelectric crystal that is typically provided with a backing pad 26 to reduce back reflections. The acoustic element 24 also provides an acoustically active surface 28 that is exposed to the fluid in the container 14. The active surface 28 may include a bonded material in a known manner that protects the crystal from adverse effects of the fluid or contamination. When the crystal is energized with a high frequency pulse, acoustic pulses are emitted into the tank fluid, reflected from the fluid surface, and detected by the sensor 10.

A resilient seal 30 such as, for example, an O-ring, is positioned in a seal groove 32 formed in the sensor body 20. The seal 30 provides a fluid-tight interface between the sensor body 20 and the flange assembly 12 to prevent fluid loss when the sensor assembly 10 is mated with the flange assembly 12. The O-ring 30 may be made, for example, of Viton material which is fuel compatible.

The flange assembly 12 is mounted in a through hole 34 formed in the container wall 14. The flange assembly 12 is preferably provided with a backing flange 36 to help rigidly support the flange assembly in the through hole 34. It will be apparent that the flange assembly will be mounted in the hole 34 in a fluid-tight manner. This can be accomplished by any suitable means 38 such as preferably using an adhesive/epoxy bonding agent, or O-rings, gaskets, welding and so on. The flange assembly 12 also includes a mounting flange 40 that is integral with a flange body 42 that can be fixedly attached to the container wall 14 such as with threaded mounting bolts 44.

The flange body 42 defines a fluid passageway 46 open to fluid in the container. The flange body has a counterbore 48 formed therein near one end of the fluid passageway. A second resilient seal 50, such as, for example, a Vitron O-ring, is seated in the counterbore 48. The flange assembly further retains an acoustic window 52, which may be a solid piece of plastic-like material such as ENVEX ™ type polyimide. The acoustic window 52 is used for impedance matching between the sensor active surface 28 and the fluid in the container. The acoustic window 52 should thus be designed with an appropriate thickness and acoustic impedance characteristics to achieve good acoustic coupling between the active surface 28 and the fluid in the container. The window preferably effects an odd multiple of the acoustic pulse quarter wavelength ($\lambda/4$) with an acoustic impedance that approximates the geometric mean of the impedances of the active surface and the fluid. According to an important aspect of the invention, the acoustic window 52 is acoustically coupled to the sensor active surface 28 by a thin film of fluid when the sensor assembly 10 is fully mated with the flange assembly 12.

As illustrated in FIG. 1, the active surface 28 preferably extends slightly axially beyond the inner distal end 54 of the sensor body 20 so as to engage the acoustic window 52 as the sensor assembly 10 is mated or inserted in the flange assembly 12.

The acoustic window 52 is movably retained in the flange body 42 by one or more ring-like wave washers 56. In the fully mated position illustrated in FIG. 1, the wave washers 56 are somewhat compressed between the window 52 and a backup ring 60 held in position with a snap ring 62. The wave washers 56 are of sufficient diameter that they do not interfere with the acoustic pulses emitted from the sensor 10 through the window 52 into the fluid passageway 46. When the sensor assembly 10 is unmated from the flange assembly 12, the wave washers exert an axial force on the acoustic window 52 and urge it into a position in which it is seated against the counterbore seal 50. Whenever the sensor assembly 10 is less than fully mated with the flange assembly 12, the window 52 and seal 50 prevent fluid from escaping the container through the fluid passageway 46 and through hole 34.

As the sensor assembly 10 is fully mated with the flange assembly 12, as in FIG. 1, the active surface 28 pushes on the acoustic window and displaces it to the position shown in FIG. 1. Fluid is able to flow between the active surface 28 and the acoustic window 52 to provide acoustic coupling between those elements. In order to facilitate this acoustic coupling, the inner end of the flange body 42 is provided with one or more cross ports 58. The ports 58 are preferably positioned axially behind but adjacent the counterbore 48 such that a slight displacement of the acoustic window from the counterbore 48 (when the sensor 10 is fully mated with the flange assembly 12) permits fluid communication between the container interior and the active surface/window interface. Thus, the active surface 28 is wetted and acoustically coupled to the acoustic window 52 by the fluid in the container. The ports are preferably used because the acoustic window is diametrically sized close to the inner diameter size of the counterbore 48. Thus, fluid flow would be less effective without the ports or other fluid path outside the periphery of the window 52. For example, instead of ports, channels could be formed in the flange body 42 to permit fluid to flow from the container interior to the active surface/window interface. Alternatively, the window periphery could be provided with notches (not shown) to channel fluid to the interface region. These are but a few examples of the many ways of enhancing the wetting action of the active surface/window interface.

As illustrated in FIG. 1, the acoustic window 52 preferably is provided with a raised bead or other structure 64 that axially separates the active surface 28 and the window 52. For clarity, the amount of separation is exaggerated in FIG. 1. The interface between the active surface and window in practice will be quite small, for example on the order of less than $\lambda/10$ at a transmit frequency of one megahertz, such that the fluid provides a thin film-like acoustic coupling therebetween. With reference to FIGS. 2A and 2B, other embodiments are shown for the acoustic window 52 to facilitate the fluid flow at the interface to the active surface. In FIG. 2A, radial serrations 70 are provided in the window interface region 72. Fluid can thus flow along the serrations to provide the acoustic coupling with the sensor 10 active surface. The window region 72 preferably is the same size as the active surface 28, thus permitting a peripheral reinforced region 74 to engage the wave washers 56. In the embodiment of FIG. 2B, the window 52 is provided with raised ridges 76 that separate the active surface 28 from the window 52 just enough to permit a fluid interface. Again, the peripheral portion of the window can thus be reinforced to engage the wave washers 56. As illustrated in FIG. 3, the window periphery may be provided with foot extensions 80 against which the wave washers 56 exert the sealing displacement force. These extensions 80 are notched as at 82 to prevent fluid from being trapped by the window 52.

As stated, the wall 14 may be the bottom tank wall of an aircraft fuel tank. By appropriate selection of dimensions, the invention provides a mounting arrangement by which the active surface 28 is positioned, when the sensor 10 is fully mated with the flange assembly 12, at or near the very bottom of the tank yet can be easily wetted for low fuel level readings. The sensor 10, of course, can also be easily unmated or removed from the flange assembly 12 without significant loss of fluid from the container.

Another important aspect of the present invention is that the acoustically active element 24 of the sensor 10 can be self-wetted and acoustically coupled by the container fluid to the impedance matching window 52 without the need for an acoustic gel at the interface. This wet interface technique also avoids the need for a rigid bonded acoustic coupling between the active surface 28 and the window 52. This aspect of the invention and its advantages can be realized not only with the mounting arrangement illustrated herein, but also with a mounting arrangement in which the acoustic window is fixedly held in the container 14 (not shown). In such an arrangement, of course, the container should be drained before removal of the sensor because the window will not be able to slide to a fluid blocking position. The fluid acoustic coupling with the impedance matching window is still a benefit in such applications since it obviates the need for rigid bonding between the active surface and the window.

While the invention has been shown and described with respect to specific embodiments thereof, this is for the purpose of illustration rather than limitation, and other variations and modifications of the specific embodiments herein shown and described will be apparent to those skilled in the art within the intended spirit and scope of the invention as set forth in the appended claims.

We claim:

1. In combination, an acoustic fluid sensor, an acoustic window and a flange assembly for mounting said sensor and window on a fluid tank, said flange assembly having a body portion configured to extend through an opening in the tank wall in a fluid-tight manner into the tank interior, said flange assembly having a body flange that is attachable to the tank wall; said body portion having a fluid passageway therein and a port that permits fluid in the tank to flow into said passageway; said flange assembly further comprising means for retaining said acoustic window in said passageway; said sensor comprising a body that is insertable in said fluid passageway in a fluid-tight manner; said sensor further comprising an active surface acoustically coupled to said window by fluid in the tank when said sensor is fully inserted in said passageway.

2. The combination of claim 1 wherein said retaining means fixedly positions said window in said fluid passageway above at least a portion of said port.

3. The combination of claim 1 wherein said retaining means movably positions said window in said fluid passageway so as to prevent fluid loss when said sensor is less than fully inserted in said passageway.

4. The combination of claim 3 wherein said sensor repositions said acoustic window when fully inserted into said passageway whereby fluid is permitted to flow into said passageway and between said active surface and said window.

5. The combination of claim 4 wherein said retaining means comprises a counterbore in said central passageway axially spaced from said port, said retaining means comprising means for biasing said acoustic window into said counterbore.

6. The combination of claim 5 wherein said counterbore receives a resilient seal that cooperates with said acoustic window to prevent fluid loss when said sensor is less than fully inserted into said passageway.

7. The combination of claim 6 wherein said biasing means comprises a wave washer that exerts force on one surface of said acoustic window to urge an opposite surface of said window into contact with said resilient seal.

8. The combination of claim 7 wherein said resilient seal is an O-ring.

9. The combination of claim 1 wherein said acoustic window includes serrations at an interface with said sensor active surface to facilitate flow of fluid between said sensor and said window when said sensor is fully inserted into said passageway.

10. The combination of claim 1 further comprising means preventing direct abutment of said sensor active surface and said acoustic window.

11. The combination of claim 1 wherein the tank wall is a bottom fuel tank wall on an aircraft.

12. An intrusive mounting arrangement for mounting an acoustic sensor to the wall of a fluid tank, said mounting arrangement comprising a flange assembly attachable to the tank wall, said sensor having an acoustic element and further being mateable and unmateable with said flange assembly; said flange assembly comprising an acoustic window and means for biasing said window to a first position when said sensor is unmated to prevent loss of fluid and for permitting said sensor to displace said window from said first position when mated to said flange assembly to permit container fluid to couple said acoustic element and said window acoustically.

13. The mounting arrangement of claim 12 wherein said flange assembly further comprises a port that is blocked to the tank exterior when said sensor is unmated and permits fluid to wet said acoustic element when said sensor is mated to said flange assembly.

14. The mounting arrangement of claim 13 wherein said biasing means comprises resilient means that positions said window against a seal means axially spaced from said port.

15. The mounting arrangement of claim 14 wherein said resilient means is a wave washer.

16. The mounting arrangement of claim 12 wherein said acoustic window includes means for facilitating flow of fluid between said acoustic element and said window when said sensor is mated to said flange assembly.

17. A method for intrusively mounting an acoustic sensor in a fluid tank comprising the steps of:
 a. mounting a flange assembly having a fluid passageway at a through hole in the fluid tank in a fluid-tight manner;
 b. sealing the flange assembly passageway to prevent fluid loss by positioning a acoustic window means to block said passageway when the sensor is uncoupled from the flange assembly; and
 c. displacing said blocking means when the sensor is coupled to the flange assembly to permit fluid to wet an acoustic element of the sensor.

18. The method of claim 17 wherein the step of displacing said window includes acoustically coupling an sensor acoustic element with said acoustic window with fluid when the sensor is coupled to the flange assembly.

19. The method of claim 18 wherein the step of sealing the flange assembly is performed using a wave washer to urge said acoustic window against a seal to block fluid loss from the tank through the flange assembly when the sensor is uncoupled.

20. An intrusive mounting arrangement for mounting a sensor on a fluid tank, the mounting arrangement comprising a flange assembly attachable to the tank wall and having a fluid passageway therein, the sensor being adapted to mate and unmate with the flange assembly in the fluid passageway, the sensor being wetted by fluid when mated to the flange assembly and the flange assembly comprising means for preventing fluid loss when the sensor is unmated therefrom, wherein the preventing means comprises an acoustic window disposed in the fluid passageway, and means for permitting the sensor to be acoustically coupled to the window by tank fluid when the sensor is mated with the flange assembly.

21. The mounting arrangement of claim 20 wherein the sensor is an acoustic sensor and the preventing means comprises an acoustic window that blocks a fluid port when the sensor is unmated and permits fluid communication between the tank interior and the fluid passageway through the port when the sensor is mated to the flange assembly.

22. The mounting arrangement of claim 21 wherein the preventing means further comprises means for positioning the window in a first position when the sensor is unmated; wherein the sensor displaces the window from the first position when the sensor is mated.

23. An intrusive mounting arrangement for mounting an acoustic transducer in a fluid container, said transducer being of the type that uses an acoustically active element and an acoustic window, said mounting arrangement comprising means for intrusively mating and unmating said transducer with the fluid container, and means for providing a wet interface between said active element and said window using fluid in the container.

24. The mounting arrangement of claim 23 further comprising means for preventing fluid loss from the container when the sensor is unmated.

* * * * *